United States Patent
Sudilovsky et al.

(10) Patent No.: US 6,187,752 B1
(45) Date of Patent: Feb. 13, 2001

(54) METHOD FOR TREATING SCHIZOPHRENIA EMPLOYING AN ACE INHIBITOR

(75) Inventors: Abraham Sudilovsky, Lawrenceville, NJ (US); Joram Feldon, Tel Aviv; Ina Weiner, Patach-Tikva, both of (IL); A. David Smith; John N. P. Rawlins, both of Oxford (GB)

(73) Assignee: E.R. Squibb & Sons, Inc., Princeton, NJ (US)

( * ) Notice: Under 35 U.S.C. 154(b), the term of this patent shall be extended for 0 days.

(21) Appl. No.: 07/758,645

(22) Filed: Sep. 12, 1991

Related U.S. Application Data (63) Continuation-in-part of application No. 07/164,694, filed on Mar. 7, 1988, now abandoned.

(51) Int. Cl.[7] .......................... A61K 38/00; A61K 38/16; A61K 31/67; C07F 9/02
(52) U.S. Cl. .................. 514/19; 514/89; 514/91; 514/92; 514/94; 514/171; 514/212; 514/218; 514/312; 514/338; 514/249; 514/255; 514/278; 514/318; 514/343; 514/409; 514/422; 514/423; 514/616; 548/413
(58) Field of Search .................... 514/19, 7, 89, 514/91, 92, 94, 171, 212, 218, 312, 338, 223.5, 249, 255, 278, 318, 343, 409, 422, 423, 616, 692.3; 548/413

(56) References Cited

U.S. PATENT DOCUMENTS

| | | | |
|---|---|---|---|
| 4,168,267 | * | 9/1979 | Petrillo, Jr. ............. 548/413 |
| 4,186,268 | * | 1/1980 | Petrillo, Jr. ............. 548/413 |
| 4,652,641 | | 3/1987 | Parsons . |
| 4,912,096 | * | 3/1990 | Sudilovsky . |
| 4,931,430 | * | 6/1990 | Sudilovsky . |
| 5,015,633 | * | 5/1991 | Sudilovsky . |

OTHER PUBLICATIONS

Drug Intell. Clin. Pharm., 15(12): 932–939, Ed. by Jackson & Cardoni, 1981.*
Petrillo et al., Medical Research Reviews, 2(1): 1–41, 1982.*
Merck Manual, 16th ed., Merck Research Laboratories, Rahway, NJ, pp. 1638–1639 and 1614–1620 (1992).*
Sebastian, C.S., et al., 1990, Biological Psychiatry, vol. 27, "Comparison of enalapril and captopril in the management of self–induced water intoxication", pp. 787–790.*
Wahlbeck, K., et al., 1993, Schizophrenia Research, vol. 9, "Elevated angiotensin–coverting enzyme (kininase II) in the cerebrospinal fluid of neuroleptic–treated schizophrenic patients", pp. 77–82.*
Vieweg, W.V.R., et al., 1997, CNS Drugs, vol. 7, "Polydipsia–hyponatremia syndrome, edipemiology, clinical features and treatment", pp. 121–138.*
Greendyke, R.M., et al., 1998, Neurophsychopharmacology, vol. 18, "Polydipsia in chronic psychiatric patients: therapeutic trials of clonidine and enalapril", pp. 272–281.*
Gray et al., *Behavioral and Brian Sciences*, 14: 1–84, 1991.*
Baruch et al., *The Journal of Nervous and Mental Disease*, 176 (10): 598–605, 1988.*
Sudilovsky, A., et al., "Attenuation of Apomorphine Induced Stereotypy by Captopril Pretreatment," presented at the 13th Annual Meeting of the Society for Neuroscience, Nov. 6 to 11, 1983, Boston, MA., Abstracts, vol. 9, Part 1, p. 132.

(List continued on next page.)

Primary Examiner—Ponnathapu Achutamurthy
Assistant Examiner—William W. Moore
(74) Attorney, Agent, or Firm—Burton & Rodney (57) ABSTRACT

A method is provided for treating schizophrenia in a mammalian species by administering an ACE inhibitor, such as captopril, alone or with a neuroleptic such as cholecystokinin, fluphenazine or haloperidol.

20 Claims, 2 Drawing Sheets

OTHER PUBLICATIONS

Parmigiani, "Evening Primrose Oil (Efamol) and Captopril in Schizophrenia: A Preliminary Report," Clinical Uses of Essential Fatty Acids, pp. 209–214, 1982 Eden Press, Inc.

Lawson et al, "Effects of Captopril on Psychosis and Disturbed Water Regulation," Psychopharmacology Bulletin, 1st Quarter 1988, Vo. 24, No. 1, pp. 176–178, presented at Annual NCDEU Meeting (May 26–28, 1987).

"Does captopril elevate mood?" TIPS—Sep. 1987 (vol. 8), pp. 329–330.

* cited by examiner

METHOD FOR TREATING SCHIZOPHRENIA EMPLOYING AN ACE INHIBITOR

REFERENCE TO OTHER APPLICATIONS

This application is a continuation-in-part of U.S. application Ser. No. 07/164,694 filed Mar. 7, 1988, and now abandoned.

FIELD OF THE INVENTION

The present invention relates to a method for treating schizophrenia in mammalian species by administering an ACE inhibitor, such as captopril, ceronapril, zofenopril or fosinopril, alone or in combination with a neuroleptic or antipsychotic drug.

BACKGROUND OF THE INVENTION

U.S. Pat. Nos. 4,046,889 and 4,105,776 to Ondetti et al disclose proline derivatives which are angiotensin converting enzyme (ACE) inhibitors including captopril.

U.S. Pat. No. 4,168,267 to Petrillo discloses phosphinylalkanoyl prolines which are ACE inhibitors.

U.S. Pat. No. 4,337,201 to Petrillo discloses phosphinylalkanoyl substituted proline ACE inhibitors which includes fosinopril.

The Petrillo patent covers fosinopril.

U.S. Pat. No, 4,432,971 to Karanewsky et al discloses phosphonamidate substituted amino or imino acids which are angiotensin converting enzyme inhibitors.

U.S. Pat. No. 4,374,829 discloses carboxyalkyl dipeptide derivatives which are said to be angiotensin converting enzyme-inhibitors which includes enalapril.

U.S. Pat. No. 4,452,790 to Karanewsky et al is directed to phosphonate substituted amino or imino acids and salts thereof which are ACE inhibitors which includes (S)-1-[6-amino-2-[[hydroxy(4-phenylbutyl)phosphinyl]oxy]-1-oxohexyl]-L-proline or ceronapril.

U.S. Pat. No. 4,316,906 to Ondetti et al discloses ether and thioether mercaptoacyl prolines which are ACE inhibitors which includes zofenopril.

Sudilovsky, A., et al., "Attenuation of Apomorphine Induced Stereotypy by Captopril Pretreatment," presented at the 13th Annual Meeting of the Society for Neuroscience, Nov. 6 to 11, 1983, Boston, Mass., Abstracts, Vol. 9, Part 1, page 132, disclose that captopril appears to attenuate apomorphine-induced stereotypy in rats which effect may be explained by captopril-induced alterations in endogenous modulators or antagonists of the dopamine receptor.

DESCRIPTION OF THE INVENTION

In accordance with the present invention, a method is provided for treating schizophrenia in mammalian species wherein an angiotensin converting enzyme inhibitor is systemically, such as orally or parenterally, administered in an amount effective to prevent or treat schizophrenia. The angiotensin converting enzyme inhibitor may be administered alone or in combination with a neuroleptic or antipsychotic drug to treat schizophrenia (whether acute episodes or recurrence thereof).

Where the angiotensin converting enzyme (ACE) inhibitor is employed in combination with a neuroleptic or antipsychotic drug, the ACE inhibitor will be employed in a weight ratio to the neuroleptic or antipsychotic drug of within the range of from about 0.0001:1 to about 1000:1 and preferably from about 0.001:1 to about 25:1.

The angiotensin converting enzyme inhibitor which may be employed herein includes substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, carboxyalkyl dipeptide derivatives, such as any of those disclosed in European Patent Application 0 012 401 mentioned above, with N-(1-ethoxycarbonyl-3-phenylpropyl)-L-alanyl-L-proline, that is, enalapril, being preferred.

Other examples of angiotensin converting enzyme inhibitors suitable for use herein include any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline (ceronapril) being preferred, phosphinylalkanoyl prolines disclosed in U.S. Pat. No. 4,168,267 mentioned above, mercaptoacyl derivatives of substituted prolines disclosed in U.S. Pat. No. 4,316,906 with zofenopril being preferred, any of the phosphinylalkanoyl substituted prolines disclosed in U.S. Pat. No. 4,337,201 discussed above, with fosinopril being preferred, and the phosphonamidates disclosed in U.S. Pat. No. 4,432,971 discussed above.

Other examples of ACE inhibitors that may be employed herein include Beecham's BRL 36,378 as disclosed in European patent Nos. 80822 and 60668; Chugai's MC-838 disclosed in CA. 102:72588v and Jap. J. Pharmacol. 40:373 (1986); Ciba-Geigy's CGS 14824 (3-([1-ethoxycarbonyl-3-phenyl-(1S)-propyl]-amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in Eur. Therap. Res. 39:671 (1986); 40:543 (1986); ramipril (Hoechst) disclosed in Eur. Patent No. 79-022 and Curr. Ther. Res. 40:74 (1986); Ru 44570 (Hoechst) disclosed in Arzneimittelforschung 35:1254 (1985), cilazapril (Hoffman-LaRoche) disclosed in J. Cardiovasc. Pharmacol. 9:39 (1987); $R_O$ 31-2201 (Hoffman-LaRoche) disclosed in FEBS Lett. 165:201 (1984); lisinopril (Merck) disclosed in Curr. Therap. Res. 37:342 (1985) and Eur. patent appl. No. 12-401, indalapril (delapril) disclosed in U.S. Pat. No. 4,385,051; rentiapril (fentiapril, Santen) disclosed in Clin. Exp. Pharmacol. Physiol. 10:131 (1983); indolapril (Schering) disclosed in J. Cardiovasc. Pharmacol. 5:643, 655 (1983); spirapril (Schering) disclosed in Acta. Pharmacol. Toxicol. 59 (Supp. 5):173 (1986); perindopril (Servier) disclosed in Eur. J. Clin. Pharmacol. 31:519 (1987); quinapril (Warner-Lambert) disclosed in U.S. Pat. No. 4,344,949 and CI 925 (Warner-Lambert) ([3S-[2[R(*)R(*)]] 3R(*)]-2-[2-[[1-(ethoxy-carbonyl)-3-phenylpropyl]amino[-1-oxopropyl]-1,2,3,4-tetrahydro-6,7-dimethoxy-3-isoquinolinecarboxylic acid HCl) disclosed in Pharmacologist 26:243, 266 (1984), WY-44221 (Wyeth) disclosed in J. Med. Chem. 26:394 (1983).

The disclosure of the above-mentioned patents and other references are incorporated herein by reference.

Examples of neuroleptics or antipsychotic drugs suitable for use herein to be employed in combination with the ACE inhibitor include, but are not limited to fluphenazine hydrochloride, fluphenazine decanoate, haloperidol, prochlorperazine, loxapine succinate, loxapine hydrochloride, thioridazine hydrochloride, molindone hydrochloride, thiothixene, thiothixene hydrochloride, trifluoperazine hydrochloride, chlorprothixene, chlorprothixene lactate and/or hydrochloride, chlorpromazine, perphenazine and/or amitriptyline hydrochloride, and/or cholecystokinin.

In carrying out the method of the invention, the angiotensin converting enzyme inhibitor alone or in combination with the neuroleptic or antipsychotic drug may be incorporated in a single conventional dosage form or each compound may be incorporated into a separate conventional dosage form to be taken at the same time. The dosage forms may comprise conventional oral forms, rectal forms or parenteral forms, such as tablets, capsules, suppositories, powders, ampoules, elixirs, suspensions, solutions, syrups, sustained release preparations and fluid injectable forms, such as sterile solutions. Oral dosage forms are preferred, although parenteral forms, such as intramuscular, intraperitoneal or intravenous forms are quite satisfactory as well.

The dose administered must be carefully adjusted according to age, weight and condition of the patient, as well as the route of administration, dosage form and regimen and the desired result.

Thus, for oral administration, a satisfactory result may be obtained employing the ACE inhibitor in an amount within the range of from about 0.01 mg/kg to about 100 mg/kg and preferably from about 0.1 mg/kg to about 25 mg/kg, and when employing ceronapril preferably from about 0.01 to about 10 mg/kg, alone or in combination with the neuroleptic or antipsychotic in an amount within the range of from about 0.01 mg/kg to about 100 mg/kg and preferably from about 0.1 mg/kg to about 25 mg/kg with the ACE inhibitor and neuroleptic or antipsychotic being employed together in the same oral dosage form or in separate oral dosage forms taken at the same time.

A preferred oral dosage form, such as tablets or capsules, will contain the ACE inhibitor in an amount of from about 1 to about 500 mg, preferably from about 125 to about 200 mg, and more preferably from about 25 to about 150 mg, and when employing ceronapril perferably from about 1 to about 50 mg, alone or with the neuroleptic or anti-psychotic in an amount of from about 1 to about 350 mg, preferably from about 2 to about 200 mg, and more preferably from about 30 to about 150 mg.

For parenteral administration, the ACE inhibitor will be employed in an amount within the range of from about 0.001 mg/kg to about 10 mg/kg and preferably from about 0.01 mg/kg to about 1 mg/kg, and when employing ceronapril preferably from about 0.005 to about 5 mg/kg, alone or with the neuroleptic or antipsychotic in an amount within the range of from about 0.005 mg/kg to about 20 mg/kg and preferbly from about 0.01 mg/kg to about 2 mg/kg.

The composition described above may be administered in the dosage forms as described above in single or divided doses of one to four times daily. It may be advisable to start a patient on a low dose combination and work up gradually to a high dose combination.

Tablets of various sizes can be prepared, e.g., of about 50 to 700 mg in total weight, containing one or both of the active substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending one or the combination of active substance in a conventional liquid vehicle acceptable for pharmaceutical administration so as to provide the desired dosage in one to four teaspoonsful.

Such dosage forms can be administered to the patient on a regimen of one to four doses per day.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

Fixed combinations of ACE inhibitor and neuroleptic or antipsychotic are more convenient and are preferred, especially in tablet or capsule form for oral administration.

In formulating the compositions of this invention, the active substances, in the amounts described above, are compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

Many of the active substances described above form commonly known, pharmaceutically acceptable salts such as alkali metal and other common basic salts or acid addition salts, etc. References to the base substances are therefore intended to include those common salts known to be substantially equivalent to the parent compound.

The following Examples represent preferred embodiments of the present invention.

EXAMPLE 1

A ceronapril formulation suitable for oral administration for treating schizophrenia is set out below.

1000 tablets each containing 10 mg of ceronapril were produced from the following ingredients.

| | |
|---|---|
| Ceronapril | 10 g |
| Corn starch | 50 g |
| Gelatin | 7.5 g |
| Avicel (microcrystalline cellulose) | 25 g |
| Magnesium stearate | 2.5 g |

The ceronapril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 10 mg of active ingredient which is used for treating schizophrenia.

EXAMPLE 2

By substituting 100 g of captopril for the ceronapril in Example 1, 1000 tablets each containing 10 mg of captopril are produced which is useful in treating schizophrenia.

EXAMPLE 3

1000 tablets each containing 20 mg of ceronapril are produced from the following ingredients:

| | |
|---|---|
| Ceronapril | 20 g |
| Lactose | 100 g |
| Avicel | 150 g |
| Corn starch | 50 g |
| Magnesium stearate | 5 g |

The ceronapril, lactose and Avicel are admixed, then blended with the corn starch. Magnesium stearate is added. The dry mixture is compressed in a tablet press to form 1000 505 mg tablets each containing 20 mg of active ingredient. The tablets are coated with a solution of Methocel E 15 (methyl cellulose) including as a color a lake containing yellow #6. The resulting tablets are useful in treating schizophrenia.

EXAMPLE 4

Two piece #1 gelatin capsules each containing 20 mg of captopril are filled with a mixture of the following ingredients:

| | |
|---|---|
| Captopril | 20 mg |
| Magnesium stearate | 7 mg |
| USP lactose | 193 mg |

The resulting capsules are useful in treating schizophrenia.

EXAMPLE 5

An injectable solution for use in treating schizophrenia is produced as follows:

| | |
|---|---|
| Ceronapril | 50 mg |
| Methyl paraben | 5 mg |
| Propyl paraben | 1 mg |
| Sodium chloride | 25 g |
| Water for injection qs. | 5 l |

The ceronapril, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 10 mg of active ingredient per ml of solution for injection.

EXAMPLE 6

Tablets for use in treating schizophrenia are prepared as described in Example 1 except that enalapril or captopril is used in place of ceronapril.

EXAMPLE 7

An injectable for use in treating schizophrenia is prepared as described in Example 5 except that captopril or enalapril is employed in place of ceronapril.

EXAMPLE 8

A zofenopril formulation suitable for oral administration in treating schizophrenia is set out below.

1000 tablets each containing 100 mg of zofenopril are produced from the following ingredients.

| | |
|---|---|
| [1(S),4(S)]-1-[3-(benzoylthio)-2-methyl-1-oxopropyl-4-(phenylthio)-L-proline (zofenopril) | 100 g |
| Corn starch | 50 g |
| Gelatin | 7.5 g |
| Avicel (microcrystalline cellulose) | 25 g |
| Magnesium stearate | 2.5 g |

The zofenopril and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 100 mg of active ingredient which is used for treating schizophrenia.

EXAMPLE 9

By substituting 100 g of fosinopril for the zofenopril in Example 8, 1000 tablets each containing 100 mg of the fosinopril are produced which is useful in treating schizophrenia.

EXAMPLE 10

1000 tablets each containing 200 mg of fosinopril are produced from the following ingredients:

| | |
|---|---|
| Fosinopril | 200 g |
| Lactose | 100 g |

-continued

| | |
|---|---|
| Avicel | 150 g |
| Corn starch | 50 g |
| Magnesium stearate | 5 g |

The fosinopril, lactose and Avicel are admixed, then blended with the corn starch. Magnesium stearate is added. The dry mixture is compressed in a tablet press to form 1000 505 mg tablets each containing 200 mg of active ingredient. The tablets are coated with a solution of Methocel E 15 (methyl cellulose) including as a color a lake containing yellow #6. The resulting tablets are useful in treating schizophrenia.

EXAMPLE 11

Tablets for use in treating schizophrenia are prepared as described in Example 1 except that 1-[N-[hydroxy(4-phenylbutyl)phosphinyl]-L-alanyl-L-proline, disodium salt (prepared as described in U.S. Pat. No. 4,432,971) is used in place of captopril.

EXAMPLE 12

An injectable for use in treating schizophrenia is prepared as described in Example 5 except that 1-[N-[hydroxy(4-phenylbutyl)phosphinyl]-L-alanyl-L-proline, disodium salt (prepared as described in U.S. Pat. No. 4,432,971) is used in place of captopril.

EXAMPLE 13

A ceronapril-fluphenazine hydrochloride formulation suitable for oral administration in the treatment of schizophrenia is set out below.

1000 tablets each containing 10 mg of ceronapril and 5 mg of fluphenazine hydrochloride are produced from the following ingredients:

| | |
|---|---|
| Ceronapril | 10 g |
| Fluphenazine hydrochloride | 5 g |
| Corn starch | 50 g |
| Gelatin | 7.5 g |
| Avicel (microcrystalline cellulose) | 25 g |
| Magnesium stearate | 2.5 g |

The ceronapril, fluphenazine hydrochloride and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 10 mg of ceronapril and 5 mg fluphenazine hydrochloride which is used for treating schizophrenia.

EXAMPLE 14

By substituting 100 g of captopril for the ceronapril and thioridazine for the fluphenazine HCl in Example 13, 1000 tablets each containing 10 mg of captopril and 10 mg of thioridazine are produced which is useful in treating schizophrenia.

EXAMPLE 15

1000 tablets each containing 20 mg of ceronapril and 10 mg cholecystokinin are produced from the following ingredients:

| | |
|---|---|
| Ceronapril | 20 g |
| Cholecystokinin | 10 g |
| Lactose | 100 g |
| Avicel | 150 g |
| Corn starch | 50 g |
| Magnesium stearate | 5 g |

The ceronapril, cholecystokinin, lactose and Avicel are admixed, then blended with the corn starch. Magnesium stearate is added. The dry mixture is compressed in a tablet press to form 1000 505 mg tablets each containing 200 mg of captopril and 10 mg of cholecystokinin. The tablets are coated with a solution of Methocel E 15 (methyl cellulose) including as a color a lake containing yellow #6. The resulting tablets are useful in treating schizophrenia.

EXAMPLE 16

Two piece #1 gelatin capsules each containing 25 mg of enalapril and 10 mg of loxapine HCl are filled with a mixture of the following ingredients:

| | |
|---|---|
| Enalapril | 25 mg |
| Loxapine HCl | 10 mg |
| Magnesium stearate | 7 mg |
| USP lactose | 193 mg |

The resulting capsules are useful in treating schizophrenia.

EXAMPLE 17

An injectable solution for use in treating schizophrenia is produced as follows:

| | |
|---|---|
| Ceronapril | 50 mg |
| Haloperidol | 5 mg |
| Methyl paraben | 5 g |
| Propyl paraben | 1 g |
| Sodium chloride | 25 g |
| Water for injection qs. | 5 L |

The ceronapril, haloperidol, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml of solution in a concentration of 10 mg of ceronapril and 5 mg of haloperidol per ml of solution for injection.

EXAMPLE 18

Tablets for use in treating schizophrenia are prepared as described in Example 13 except that captopril or enalapril is used in place of ceronapril.

EXAMPLE 19

Tablets for use in treating schizophrenia are prepared following the procedure of Example 13 except that zofenopril is employed in place of ceronapril.

EXAMPLE 20

Tablets for use in treating schizophrenia are prepared following the procedure of Example 13 except that fosinopril is employed in place of ceronapril.

EXAMPLE 21

Tablets for use in treating schizophrenia are prepared following the procedure of Example 13 except that alacepril is employed in place of ceronapril.

EXAMPLE 22

The following experiments were designed to investigate the neuroleptic-like action of ceronapril, using an animal model that simulates a cognitive dysfunction characteristic to certain forms of schizophrenia, namely, attentional deficit. The model is based on the paradigm of latent inhibition (LI), in which non-reinforced pre-exposure to a stimulus retards subsequent conditioning to that stimulus when it is paired with a reinforcer (Lubow, R. E., (1973) "Latent inhibition" Psychol. Bull. 79:398–407). For example, if an animal is pre-exposed to a series of tones, these tones lose their capability to enter into associations with other stimuli, such as shock, or responses such as shuttle avoidance. This decremental process is considered to reflect a process of learning not to attend to, ignore, or tune out irrelevant stimuli (Lubow, et al. (1981). "Conditioned attention theory." In: Bower GH (ed.), The Psychology of Learning and Motivation (Vol. 15) New York, Academic Press; Mackintosh, N. J. (1973). "Stimulus selection: Learning to ignore stimuli that predict no change in reinforcement." In: Hinde R A, Hinde J S (eds.), Constraints on Learning: Limitations and Predispositions. Cambridge, Academic Press; Mackintosh, N. J. (1975). "A theory of attention: Variations in the associability of stimuli with reinforcement." Psychol. Rev. 82:276–298; Mackintosh, N. J. (1983). Conditioning and Associative Learning. New York, Oxford University Press; Moore, J. W. (1979). "Brain processes and conditioning." In: Dickinson A., Boakes R A (eds.), Mechanisms of Learning and Motivation: A Memorial Volume for Jerzy Konorski. Hillsdale, Erlbaum.

The relevance of LI to the clinical syndrome has been documented as follows: Dating back to Bleuler's (Bleuler, E. (1911). "Dementia Praecox or the Group of Schizophrenias." New York, International Universities Press) description of schizophrenia as the loss of "selectivity which normal attention ordinarily exercises among the sensory impressions", attentional deficit has been the most emphasized feature of schizophrenia. Most often, such deficit has been described as an inability to ignore irrelevant or unimportant stimuli (Anscombe, F. (1987). "The disorder of consciousness in schizophrenia." Schizophren. Bull. 2:241–260). In addition, the amelioration of schizophrenic symptoms with neuroleptic treatment was shown to be related to the normalization of attentional processes (Asarnow, R. F. et al., (1988). "Differential effect of low and conventional doses of fluphenazine on schizophrenic outpatients with good or poor information processing abilities." Arch. Gen. Psychiatry 45:822–826; Braff, D. L. et al., (1982). "Effect of antipsychotic medication on speed of information processing in schizophrenic patients." Am. J. Psychiatry 139:1127–1130; Kornetzky, C. (1972). "The use of simple test of attention as a measure of drug effects in schizophrenic patients." Psychopharmacology 24:99–106; Maloney, M. P. et al., (1976). "Auditory attention in process and reactive schizophrenics." Biol. Psychiatry 11:325–335; Oltmanns, T. F. et al., (1978). "The effect of antipsychotic medication and diagnostic criteria on distractability in schizophrenia." J. Psychiatr. Res. 14;81–91; Rappaport, M. J. et al., (1971). "Phenothiazine effects on auditory signal detection in paranoids and paranoid schizophrenics." Science 174:723–725; and Spohn, H. E., et al., (1977). "Phenothiazine effects on psychological and psychopharmacological dysfunction in chronic schizophrenics." Arch. Gen. Psychiatry 34:633–644).

In a series of animal experiments, it was demonstrated that: 1. LI is disrupted by the dopamine-releasing psychotomimetic drug, amphetamine (Solomon, P. R. et al., (1981). "Disrupted latent inhibition in the rat with chronic amphetamine or haloperidol induced super-sensitivity: Relationship in schizophrenia attention disorder." Biol. Psychiatry 16:519–537; Weiner, I. et al., (1981). "Chronic amphetamine and latent inhibition." Behav. Brain Res. 2:285–286; Weiner, I. et al., (1984). "Abolition of the expression but not the acquisition of latent inhibition by chronic amphetamine in rats." Psychopharmacology 83:194–199; and Weiner, I. et al., (1988). "Disruption of latent inhibition by acute administration of low doses of amphetamine." Pharmacol. Biochem. Behav. 30:871–878). The behavioral effects of amphetamine administration in animals have been long considered to provide an animal model of psychosis (Kokkinidis, L. et al., (1980). "Amphetamine models of paranoid schizophrenia: An overview and elaboration of animal experimentation." Psychol. Bull. 88:551–579; Robinson, T. E. et al., (1986). "Enduring changes in brain and behavior produced by chronic amphetamine administration: A review and evaluation of animal models of amphetamine psychosis." Brain Res. Rev. 11:157–198; and Segal, D. S. et al., (1983). "Animal models of stimulant-induced psychosis." In: Creese, I (ed), Stimulants: Neurochemical, Behavioral and Clinical Perspectives. New York, Raven Press), but this model has been based almost exclusively on the motor effects of this drug, i.e., locomotor activation and stereotypy. The results with LI showed that amphetamine treatments renders animals incapable of ignoring irrelevant stimuli. 2. Amphetamine-induced disruption of LI is subserved by the mesolimbic dopaminergic system (Solomon, P. R. et al., (1982). "Differential effects of microinjections of d-amphetamine into the nucleus accumbens or the caudate putamen on the rat's ability to ignore an irrelevant stimulus." Biol. Psychiatry 17:743–756; and Weiner, I. et al., (1987). "Latent inhibition is not affected by acute or chronic administration of 6 mg/kg dl-amphetamine." Psychopharmacology 91:345–351.) 3. Amphetamine induced disruption of LI is antagonized by neuroleptic drugs, chlorpromazine (Solomon, P. R. et al., (1981), supra, and haloperidol (Weiner, I. et al., (1990). "Disruption of latent inhibition by low dose of amphetamine is antagonized by haloperidol and apomorphine." J. Psychopharm. 4:255). 4. The administration of haloperidol, both acute and repeated, facilitates LI, i.e. enhances animals' ability to ignore irrelevant stimuli (Christison, G. W. et al., (1988). "Haloperidol enhancement of latent inhibition: Relation to therapeutic action?" Biol. Psychiatry 23:746–749;Feldon, J. et al., (1988). "Long-term attentional deficit in nonhandled males: Possible involvement of the dopaminergic system." Psychopharmacology 95:231–236; Feldon, J. et al. (1991b). "The latent inhibition model of schizophrenic attention disorder: Haloperidol and sulpiride enhance rat's ability to ignore irrelevant stimuli". Biol. Psychiatry, in press; Weiner, I. et al., (1987). "Facilitation of the expression but not the acquisition of latent inhibition by haloperidol in rats." Pharmacol. Biochem. Behav. 26:241–246; and Weiner, I. et al., (1987). "Facilitation of latent inhibition by haloperidol." Psychopharmacology 91:248–253). An identical facilitation of LI is obtained with the atypical neuroleptic, sulpiride (Feldon and Weiner, 1991b supra), which was shown to act preferentially on the mesolimbic dopaminergic system. These results indicated that the development of LI may reflect the operation of an attentional process which is related to attentional functions impaired in schizophrenia. In support of this suggestion, it was shown that LI is absent in acute schizophrenics tested within the first week of the beginning of a schizophrenic episode but is present in medicated schizophrenics (Baruch, I. et al., (1988). "Differential performance of acute and chronic schizophrenics in a latent inhibition task." J. Nervous Mental Disease 176:598–606; and Lubow, R. E. et al., (1987). "Latent inhibition and schizophrenia." Bull. Psychon. Soc. 25:464–467). Moreover, the disruption of LI covaried with the presence of psychosis: The acute patients themselves demonstrated normal LI six to seven weeks later, after their psychosis diminished with treatment (Baruch et al. 1988, supra).

Taken together the above data show that both acute schizophrenic patients and rats with mesolimbic dopamine overactivity exhibit a loss of LI, and that this abnormality is reversed by neuroleptic treatment. Consequently, it was proposed that the phenomenon of LI provides a viable animal model for the study of attentional deficits characteristic of schizophrenia and their amelioration by pharmacological treatments (Feldon and Weiner 1991a "An animal model of attention deficit". In: Boulton, A. A. et al (eds), Neuro-methods (Vol. 19): Animal Models in Psychiatry. New York, Humana Press; Feldon and Weiner 1991b, supra; Gray, J. A. et al., (1991). "The neuro-psychology of schizophrenia." Behav. Brain Sci., Vol. 14, pp 1–84; Weiner, I. (1990). "Neural substrates of latent inhibition: The switching model", Psychol. Bull. 108:442–461; and Weiner, I. et al., (1984) supra). As elaborated by (Feldon and Weiner (1991a) supra and Ellenbroek, B. A. et al., (1990). "Animal models with construct validity for schizophrenia." Behav. Pharmacol. 1:) the LI model of schizophrenic attention deficit has a high face and construct validity. Moreover, the facilitatory effect of neuroleptic drugs in this model provides a novel screening test for detecting anti-psychotic potential. In this context, it should be noted that the neuroleptic-induced facilitation of LI is unique in several respects: 1. It provides the first demon-stration of a facilitatory influence of neuroleptics on attention. 2. It is specific to neuroleptics, as all other pharmacological and physiological manipulations tested to date have been found either to abolish LI or to leave it intact (Weiner 1990, supra). 3. It is highly relevant to their clinical use. 4. It is obtained with both typical and atypical neuroleptics. 5. It does not rely on demonstrating interactions with some other drug. Most of the existing behavioral tests for screening neuroleptic compounds are based on DA receptor blockade by neuroleptics, and rely on neuroleptic-induced antagonism of DA-agonist-induced behaviors. As frequently noted, drug-drug tests are unlikely to identify antipsychotics which do not act via the dopaminergic system. A purely behavioral test such as LI is devoid of such a disadvantage.

Two LI procedures were designed that are uniquely sensitive for tapping facilitatory effects of drugs on attention. One procedure employs pre-exposure conditions which do not yield LI in normal animals, namely, low number of non-reinforced stimulus pre-exposures. The secondprocedure employs conventional pre-exposure parameters, but extends subsequent conditioning to a level at which normal animals cease to show LI. Using these procedures, it was showed that normal animals, as expected, failed to show LI, whereas animals treated with haloperidol or sulpiride did exhibit LI (Feldon et al., (1990). "Latent inhibition and its modulation by amphetamine in rats screened for high and low spontaneous activity." J. Psychopharm. 4:283; Feldon and Weiner 1991b, supra; Weiner and Feldon 1987, supra).

The present experiments sought to test whether ceronapril would produce a neuroleptic-like facilitatory effect on LI. LI was assessed using a conditioned emotional response (CER) procedure in rats licking for water, consisting of three stages: pre-exposure, in which the to-be-conditioned stimulus, tone, was repeatedly presented without being followed by reinforcement; conditioning, in which the pre-exposed stimulus was paired with reinforcement, shock; and test, in which LI was indexed by animals' suppression of licking during tone presentation.

Experiment 1 used a moderate level of pre-exposure, namely, 20 non-reinforced tone presentations, followed by an extended conditioning phase that included 5 tone-shock pairings. Experiment 2 used a brief pre-exposure to 5 non-reinforced tones, followed by two tone-shock pairings in conditioning. Both procedures do not yield LI in normal animals. Experiment 1 tested the effects of three doses of ceronapril: 0.005, 0.05, 0.5 mg/kg, and Experiment 2 tested the effects of only 0.05 mg/kg, which was found effective in Experiment 1. Experiment 3 used a procedure that yields LI in normal animals, consisting of forty tone pre-exposures and 2 tone-shock pairings; the effects of 0.05 mg/kg ceronapril on LI as well as on the disruption of LI produced by 1 mg/kg amphetamine were assessed.

Experiment 1

Subjects—Fifty-six male Wistar rats approximately 4 months old, were housed one to a cage under reversed cycle lighting for the duration of the experiment. Upon delivery, subjects were maintained on freely available food and water for three weeks. On the 22nd day animals were weighed and placed on a 23 hour water deprivation schedule which continued throughout the experiment.

Apparatus—The apparatus consisted-of four Campden Instruments Rodent Test Chambers (Model 410), each set in a ventilated sound-attenuating Campden Instruments Chest (Model 412). A drinking bottle could be inserted into the chamber through a 0.5 cm diameter hole located in the center of the left wall of the chamber, 2.5. cm above the grid floor. When the bottle was not present, the hole was covered by a metal lid. Licks were detected by a drinkometer circuit (Campden-Instruments drinkometer model 453). The pre-exposed to-be-conditioned stimulus was a 2.8 kHz tone produced by a Sonalert module (Model SC 628). Shock was supplied by a Campden-Instruments shock generator (Model 521/C) and shock scrambler (Model 521/S) set at 0.75 mA. Equipment programming and data recording were controlled by an IBM-compatible personal computer (Amigo-MX).

Procedure Handling—Prior to the beginning of the experiment, animals were handled for seven days, for about 2 minutes each day. The stages of the CER procedure were as follows:

Baseline—On each of five days, each animal was placed into the experimental chamber and allowed to drink for 20 minutes.

Pre-exposure (PE)—With the bottle removed, each animal was placed in the experimental chamber. The pre-exposed (PE) animals received 20 ten second tones with an inter-stimulus interval (ISI) of 60 seconds. The non-pre-exposed (NPE) animals were confined to the chamber for an identical period of time but did not receive the tone.

Conditioning—With the water-bottle removed, each animal received five tone-shock pairings, given five minutes apart. Tone parameters were identical to those used in pre-exposure. The 0.75 mA, 1 second shock immediately followed tone termination. The first tone-shock pairing was given 5 minutes after the start of the session. After the fifth pairing, animals were left in the experimental chamber for an additional 5 minutes.

Re-baseline—Each animal was given a drinking session identical to the baseline sessions. Latency to the first lick and the total number of licks were recorded for each subject.

Test—Each subject was individually placed in the chamber and allowed to drink from the bottle. When the subject completed 75 licks the tone was presented, and lasted 5 minutes. The following times were recorded: Time to first lick, time to complete licks 1–50, time to complete licks 51–75 (pre-tone) and time to complete licks 76–100 (tone-on). The times to complete licks 76–100 were subjected to logarithmic transformation to ensure that the distribution of the data is suitable for parametric analysis of variance. The stages of pre-exposure, conditioning, re-baseline and test were given 24 hours apart. Each subject was run throughout the experiment in the same chamber.

Experimental design and drug treatment—The 56 animals were randomly assigned to eight experimental groups in a 2×4 factorial design with main factors of pre-exposure (0,20) and drug (vehicle, 0.005 mg/kg, 0.05 mg/kg and 0.5 mg/kg ceronapril). The appropriate drug dose was dissolved in saline (1 ml/kg) and administered IP 30 minutes prior to the start of pre-exposure and 30 minutes prior to the start of conditioning. The re-baseline and test stages were conducted without drugs. Data of four subjects were lost due to apparatus failure one from the 0.005 mg/kg-PE group, one from 0.05 mg/kg-NPE group, one from 0.5 mg/kg-NPE group and one from 0.5 mg/kg-PE group. Thus, the final analyses were performed on the data of 52 subjects.

Figure 1:
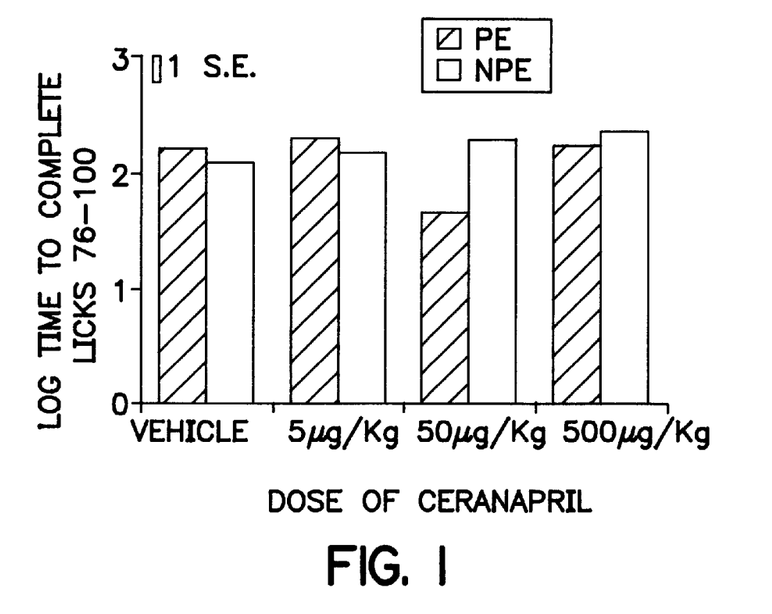
FIG. 1 is a graph showing mean log times to complete licks 76–100 in the presence of the tone for the preexposed and nonpreexposed groups in the four drug conditions: vehicle, 0.005 mg/kg, 0.05 mg/kg and 0.5 mg/kg of ceronapril.

Results—The 2×4 Anova's with main factors of pre-exposure (0,20) and drug (0.0, 0.005, 0.05, 0.5 mg/kg ceronapril) performed on the latencies to first lick and on the total number of licks 1–50, and times to complete licks 51–75 on test day, yielded no significant outcomes. FIG. 1 presents the mean log times to complete licks 76–100 in the four experimental conditions. As can be seen, in the vehicle, 0.005 mg/kg and 0.5 mg/kg conditions, both the nonpre-exposed and pre-exposed animals exhibited high degree of suppression of drinking during the presentation of the tone, i.e., showed no LI. In contrast, in the 0.05 mg/kg condition, the pre-exposed animals exhibited less suppression of drinking during tone presentation as compared to the nonpre-exposed controls, i.e., developed LI. These outcomes were supported by the 2×4 ANOVA performed on the log times to complete licks 76–100 which yielded only a significant interaction of pre-exposure x drug dose [F(3,44)=3.07, p<0.05]. Post-hoc t-tests based on the error term derived from the ANOVA revealed a significant difference between the pre-exposed and nonpre-exposed groups only in the 0.05 mg/kg ceronapril condition [t(44)=2.67, p<0.02].

Figure 2:
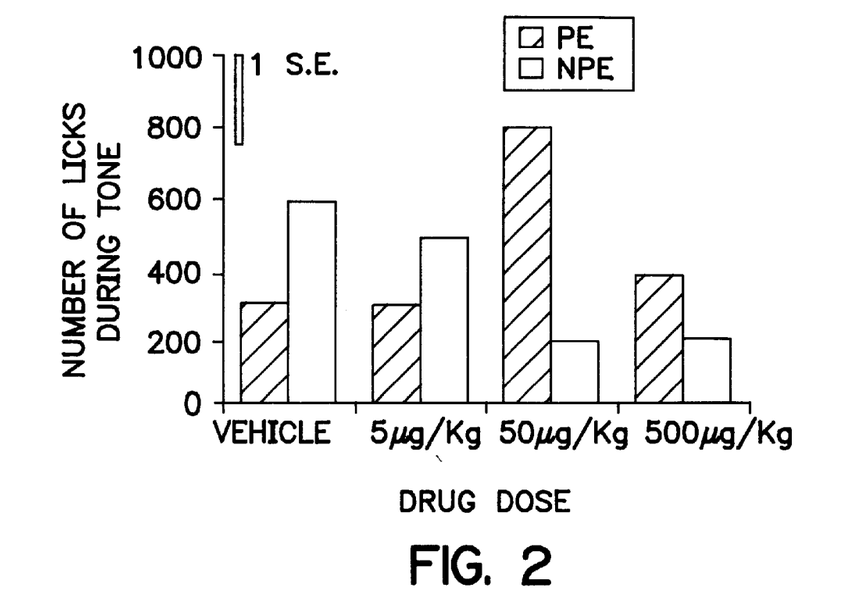
FIG. 2 is a graph showing mean number of licks during tone presentation (5 minutes) for the preexposed and non-preexposed groups in the four drug conditions: vehicle, 0.005 mg/kg, 0.05 mg/kg and 0.5 mg/kg of ceronapril.

The selective facilitatory effects of the 0.05 mg/kg dose of ceronapril on LI was also evident in the analyses of other measures recorded during test. Thus, the mean latencies to first lick during tone presentation (and standard errors) of the four experimental conditions were as follows: vehicle-NPE= 143±45; vehicle-PE=198±57; 0.005 mg/kg-NPE=182±47; 0.005 mg/kg-PE=217±43; 0.05 mg/kg-NPE=253±51; 0.05 mg/kg-PE=81±40; 0.5 mg/kg-NPE=242±44; 0.5 mg/kg-PE= 183±58. A 2×4 ANOVA performed on the mean latencies to first lick during tone presentation (latency to lick 76), yielded a significant interaction of pre-exposure x drug dose [F(3,44)=2.80, p<0.05]. Post-hoc t-tests revealed that the only drug condition in which the PE and NPE groups differed significantly was the 0.05 mg/kg dose of ceronapril; the PE group demonstrated shorter latencies than the NPE group to begin drinking during the tone. [t(44)=2.73. p<0.01]. Likewise, a 2×4 ANOVA performed on the total number of licks completed by animals in the four experimental conditions during tone presentation, yielded a significant interaction of pre-exposure x drug dose [F(3,43)= 3.07. p<0.04]. These results are depicted in FIG. 2. It is interesting to note that the NPE groups of both the 0.05 mg/kg and 0.5 mg/kg conditions had higher suppression of licking compared with the vehicle-NPE group, although this effect did not reach the acceptable level of significance. However, whereas the 0.5 mg/kg dose increased suppression also in the PE group, an opposite effect is seen with the 0.05 mg/kg dose, i.e., the PE group exhibited a significant increase of drinking as compared with the NPE group.

Experiment 2

Subjects—Forty-eight male Wistar rats as in Exp. 1.

Apparatus—As in Exp. 1

Procedure Handling and Baseline—as in Exp. 1.

Pre-exposure (PE)—As in Exp. 1 except that the pre-exposed (PE) animals were confined to the chamber for an identical period of time but did not receive the tone.

Conditioning—As in Exp. 1 except that only two tone-shock pairings were given in conditioning.

Re-baseline and Test—As in Exp. 1.

Experimental design and drug treatment—The 48 animals were randomly assigned to four experimental groups in a 2×2 factorial design with main factors of pre-exposure (0.5) and drug (vehicle, 0.05 mg/kg ceronapril). The appropriate drug dose was dissolved in saline (1 ml/kg) and administered IP 30 minutes prior to the start of pre-exposure and 30 minutes prior to the start of conditioning. The re-baseline and test stages were conducted without drugs. Data of three subjects were lost due to apparatus failure: one from the Vehicle-PE group, one from the Vehicle-NPE group and one from the 0.05 mg/kg-NPE group. Thus, the final analyses were performed on the data of 45 subjects.

Figure 3:
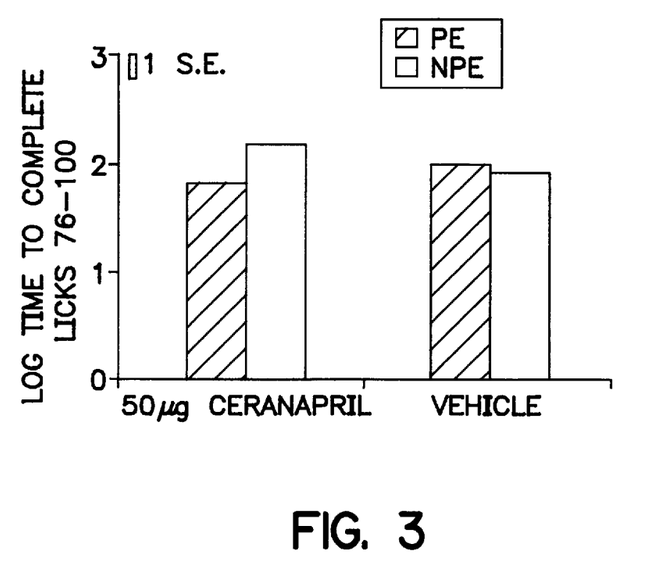
FIG. 3 is a graph showing mean log times to complete licks 76–100 in the presence of the tone for the preexposed and nonpreexposed groups in two drug conditions: vehicle and 0.05 mg/kg, ceronapril.

Results—The 2×2 ANOVA's with main factors of pre-exposure (0.5) and drug (vehicle, ceronapril 0.05 mg/kg) performed on the latencies to first lick and total number of licks on re-baseline day as well as on the latencies to first lick, time to complete licks 1–50, and times to complete licks 51–75 on test day, yielded no significant outcomes. FIG. 3 presents the mean log times to complete licks 76–100 in the vehicle and ceronapril conditions. As can be seen, LI, i.e. lower suppression of drinking during tone presentation in the PE group compared with the NPE group, was evident only in animals treated with 0.05 mg/kg of ceronapril. This outcome was supported by a 2×2 ANOVA performed on the data which yielded only a significant interaction of pre-exposure x drug [F(1,41)=4.08, p<0.05]. It should be noted that the drug led to increased suppression in the NPE group compared with the vehicle-NPE group as well as to decreased suppression of the PE group compared with the vehicle-PE group. However, both these effects have not attained the acceptable level of significance. The facilitatory effect of ceronapril was also evident in the analysis of mean latencies to first lick during tone presentation (latency to lick 76). The mean times (and standard errors of the mean) of the four experimental groups were as follows: vehicle-NPE= 132±42; vehicle-PE=153±39; 0.05 mg/kg-NPE=205±35; 0.05 mg/kg-PE=74±32. A 2×2 ANOVA yielded a significant interaction of pre-exposure x drug [F(1,41)=4.65. p<0.051, reflecting the fact that ceronapril-PE group showed a decreased latency to initiate drinking in the presence of the tone as compared to vehicle-PE group. Also in this measure there appeared a tendency, albeit non-significant for the ceronapril-NPE group to be more suppressed than the vehicle-NPE group. The analysis of total number of licks yielded no significant results, but the pattern was identical to that obtained in the other two measures.

Experiment 3

Subjects—One hundred and four male Wistar rats as in Exp. 1. The experiment contained two replications conducted two months apart, with 56 animals in the first replication and 48 animals in the second replication.

Apparatus—As in Exp. 1.

Handling and Baseline—As in Exp. 1.

Pre-exposure—As in Exp. 1 except that the pre-exposed (PE) animals received 40 ten second tones with an interstimulus interval (ISI) of 30 seconds. The nonpre-exposed (NPE) animals were confined to the chamber for an identical period of time but did not receive the tone.

Conditioning—As in Exp. 2.

Experimental design and drug treatment—The 104 animals were randomly assigned to eight experimental groups 2×4 factorial design with main factors of pre-exposure (0,40) and drug condition (vehicle, 1 mg/kg amphetamine, 0.05 mg/kg ceronapril, ceronapril+amphetamine). Each subject received two i.p. injections prior to pre-exposure and prior to conditioning. The first injection consisted of either 0.05 mg/kg ceronapril in 1 ml saline or an equivalent volume of saline and was administered 30 minutes prior to the start of pre-exposure and 30 minutes prior to conditioning. The second injection consisted of either 1.0 mg/kg d-amphetamine dissolved in saline or an equivalent volume of saline and was administered 10 minutes prior to the start of pre-exposure and 10 minutes prior to conditioning. The re-baseline and test stages were conducted without drugs. Data of six subjects were lost due to apparatus failure: two from the ceronapril-vehicle-NPE group, one from the vehicle-vehicle-PE group and three from the ceronapril-vehicle-PE group. Thus, the final analyses were performed on the data of 98 subjects.

Figure 4:
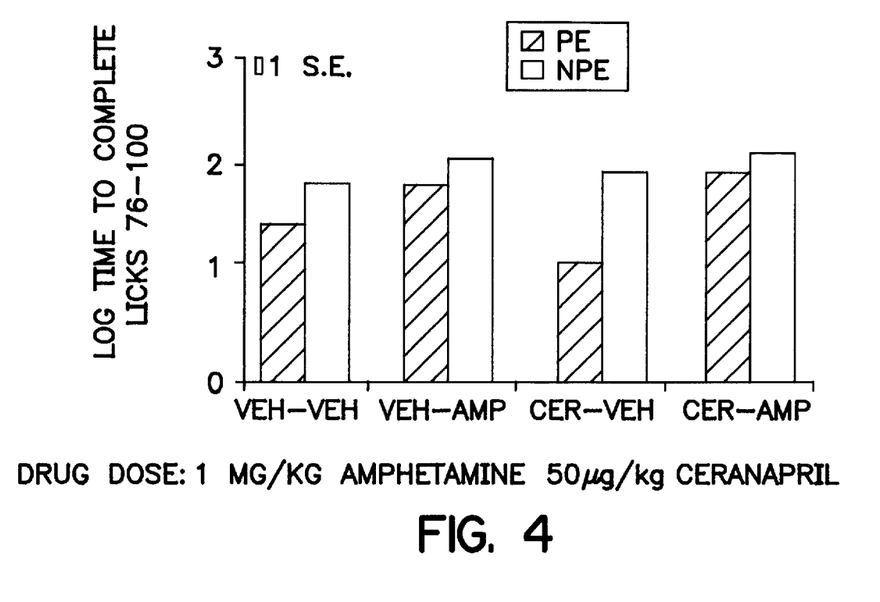
FIG. 4 is a graph showing mean log times to complete licks 76–100 in the presence of the tone for the preexposed and nonpreexposed groups in the four drug conditions: vehicle, 1 mg/kg amphetamine, 0.5 mg/kg ceronapril, and 1 mg/kg amphetamine plus 0.05 mg/kg ceronapril.

Results—2×4 ANOVA's with main effects of pre-exposure (0, 40) and drug (vehicle, amphetamine, ceronapril, ceronapril+amphetamine) performed on the latencies to first lick and the total number of licks on re-baseline day as well as on the latencies to first lick, time to complete licks 1–50, and times to complete licks 51–75 in test, yielded no significant outcomes. FIG. 4 presents the mean log times to complete licks 76–100 in the four experimental conditions. A 2×4 ANOVA performed on the data yielded a significant main effect of pre-exposure $[F(1,90)=16.80, p<0.001]$, a significant main effect of drug $[F(1,90)=6.14, p<0.001]$, and a significant interaction of pre-exposure x drug $[F(3,90)=2.80, p<0.005]$. As can be seen in FIG. 4, there were no significant differences between the four NPE groups (see bar indicating the standard error derived from the ANOVA). On the other hand, the four PE groups differed from each other, such that there was a significant LI effect in both the vehicle $[t(90)=2.00, p<0.05]$ and the ceronapril $[t(90)=4.65, p<0.001]$ conditions, but not in the amphetamine or in the ceronapril+amphetamine conditions. Furthermore, ceronapril caused a significant reduction in suppression in the PE group compared with the vehicle condition $[t(90)=2.00, p<0.005]$. Thus, ceronapril enhanced latent inhibition when administered on its own, but did not reverse the disruption of latent inhibition caused by amphetamine. The other measures, mean latency to initiate drinking during the tone and total number of licks, have yielded similar, but not quite significant patterns.

Discussion

Experiments 1 and 2 employed parameters that do not yield LI in normal animals. In Experiment 1, a moderate pre-exposure to 20 tones was followed by an intense conditioning phase with 5 tone-shock pairings, which would be expected to overwhelm any tendency to have learned to ignore the target stimulus. In Experiment 2, a brief pre-exposure to five tones was followed by a moderate conditioning phase with 2 tone-shock pairings: in this case, normal animals would be expected to have acquired only a slight tendency to ignore the target stimulus in the first place. In both these experiments it was found, as expected, that vehicle treated animals showed the same degree of response suppression whether or not they had been pre-exposed to the tone. In marked contrast, animals treated with 0.05 mg/kg ceronapril, did develop LI in both experiments: pre-exposed animals exhibited less response suppression than their nonpre-exposed counterparts. This dose of drug thus induced an ability to develop LI under conditions in which vehicle-treated animals fail to do so. Additional confirmation of ceronapril-induced enhancement of LI was obtained in Experiment 3, in which animals were given an extensive pre-exposure to 40 tones, followed by a moderate conditioning phase with two tone-shock pairings: under these conditions vehicle treated animals did develop LI, but 0.05 mg/kg ceronapril treatment produced an even greater LI effect.

It is clear that ceronapril exerts a robust facilitatory effect on LI. Furthermore, this enhancement is primarily through a drug effect in the PE condition. Thus, ceronapril-treated NPE animals exhibited suppression similar to vehicle animals, whereas the ceronapril-treated PE animals showed significantly less suppression to the tone than vehicle-PE group, resulting in an enhanced LI effect in the ceronapril-treated animals. The only other pharmacological treatments that are known to produce this pattern of effects on LI are those involving the typical or atypical neuroleptics. One feature that may be peculiar to the present compound is the very narrow range of effective doses: the upper effective limit appears to be below 0.1 mg/kg, and in pilot experiments it was found that the lower limit is around 0.025 mg/kg. Also, Costall et al. (1989) "The effects of ACE inhibitors captopril and SQ29,852 in rodent tests of recognition." Pharmacol. Biochem. Behav. 38:573–579 reported that the effects of ceronapril were observed in the rat over a narrow dose range.

While ceronapril exerted a neuroleptic-like effect on LI when given on its own it did not antagonize the disruption of LI by amphetamine (Solomon, et al. 1981; supra; Weiner, et al. 1990; supra). This restitution of LI is not shared by ceronapril when given at the present dose. However, the present data do not rule out the possibility of interactions between the effects of ceronapril and dopamine agonists. The finding can be viewed from two different perspectives: either ceronapril can be taken as being unable to block the effects of amphetamine, or amphetamine can be taken to have blocked the effects of ceronapril. If the latter view holds, then it seems possible that a higher dose of ceronapril, which would have no tendency to enhance LI in normal animals, would do so in hyperdopaminergic subjects, and thereby reinstate normal attentional learning.

The LI results are best interpreted as demonstrating that ceronapril exerts a selective cognitive enhancement effect on attentional processes, more specifically, on the ability to ignore irrelevant stimuli. As noted above, this enhancing effect mimics that obtained with neuroleptic drugs. In this context it is worth reiterating that LI is the only behavioral paradigm in which neuroleptics exert a dramatic facilitatory effect whereas all other behavioral tasks are either unaffected or impaired by these drugs.

Summary

Three experiments that used a latent inhibition (LI) procedure to investigate the effects of ceronapril on attentional processes were carried out. LI is a behavioral paradigm in which prior exposure to a stimulus with no significant consequences retards subsequent conditioning to that stimulus when it is paired with reinforcement. LI reflects a process of learning to ignore, or tune out, irrelevant stimuli, and has been suggested as an animal model of the attentional processes disrupted in the acute phase of schizophrenia. In animals, LI is disrupted by the administration of low doses of amphetamine and enhanced by the administration of neuroleptics. Ceronapril is an angiotensin converting enzyme (ACE) inhibitor that has been shown to retard the breakdown of central cholecystokinin (CCK). It has been proposed that elevation of CCK levels in the brain may possess neuroleptic-like properties. This possibility was assessed by determining the effects of ceronapril on LI using a conditioned emotional response (CER) procedure, consisting of three stages: pre-exposure, in which the to-be-conditioned stimulus, a tone, was repeatedly presented without reinforcement; conditioning, in which the pre-exposed stimulus was paired with shock; and test, where LI was indexed by animals' suppression of licking during tone presentation. In Experiment 1, twenty tone pre-exposures were given, and conditioning consisted of 5 tone-shock pairings; the effects of 0.005 mg/kg, 0.05 mg/kg and 0.5 mg/kg ceronapril compared to vehicle injections were assessed. In Experiment 2, five tone pre-exposures were given, and conditioning consisted of 2 tone-shock pairings: the effects of 0.05 mg/kg ceronapril compared to vehicle injections were assessed. Both procedures are known to be insufficient to produce LI in normal animals. In both experiments, LI was indeed absent in vehicle controls. In marked contrast, animals treated with 0.05 mg/kg ceronapril exhibited LI. Experiment 3 used a procedure that yields LI in normal animals, consisting of forty tone pre-exposures and 2 tone-shock pairings; the effects of 0.05 mg/kg ceronapril on LI as well as on the disruption of LI produced by 1 mg/kg amphetamine were assessed. Ceronapril (0.05 mg/kg) significantly enhanced LI with respect to vehicle controls. This enhancing effect was not seen in rats given 1 mg/kg amphetamine. Ceronapril thus produces effects on attentional learning that have hitherto been shown only with typical and atypical neuroleptics, and therefore possesses antipsychotic properties.

What is claimed is:

1. A method for treating schizophrenia in a mammalian species, which comprises administering to a mammalian species in need of such treatment an effective amount of an angiotensin converting enzyme inhibitor, wherein the angiotensin converting enzyme inhibitor is a phosphonate substituted amino or imino acid or salt thereof, a substituted proline derivative, a carboxyalkyl dipeptide derivative, a phosphinylalkanoyl proline derivative or a phosphonamidate derivative.

2. The method as defined in claim 1 wherein said angiotensin converting enzyme inhibitor alone or with a neuroleptic drug is administered orally or parenterally.

3. The method as defined in claim 1 wherein said angiotensin converting enzyme inhibitor alone or with a neuroleptic drug is admixed with a pharmaceutically acceptable carrier therefor.

4. The method as defined in claim 1 wherein said angiotensin converting enzyme inhibitor is a substituted proline derivative.

5. The method as defined in claim 1 wherein said angiotensin converting enzyme inhibitor is a carboxyalkyl dipeptide derivative.

6. The method as defined in claim 1 wherein said angiotensin converting enzyme inhibitor is a phosphinylalkanoyl proline derivative.

7. The method as defined in claim 1 wherein said angiotensin converting enzyme inhibitor is a phosphonamidate derivative.

8. The method as defined in claim 1 wherein said angiotensin converting enzyme inhibitor is a phosphonate substituted amino or imino acid or salt thereof.

9. The method as defined in claim 1 wherein said angiotensin converting enzyme inhibitor is captopril.

10. The method as defined in claim 1 wherein said angiotensin converting enzyme inhibitor is enalapril or lisinopril.

11. The method as defined in claim 1 wherein said angiotensin converting enzyme inhibitor is ceronapril.

12. The method as defined in claim 1 wherein said angiotensin converting enzyme inhibitor is zofenopril.

13. The method as defined in claim 1 wherein said angiotensin converting enzyme inhibitor is fosinopril.

14. The method as defined in claim 11 wherein said angiotensin converting enzyme inhibitor is ceronapril and is administered systemically in an amount within the range of from about 0.1 to about 500 mg one to four times a day.

15. A method for treating schizophrenia in a mammalian species, which comprises administering to a mammalian species in need of such treatment an effective amount of an angiotensin converting enzyme inhibitor, wherein the angiotensin converting enzyme inhibitor is a phosphonate substituted amino or imino acid or salt thereof, a substituted proline derivative, a carboxyalkyl dipeptide derivative, a phosphinylalkanoyl proline derivative or a phosphonamidate derivative, in combination with a neuroleptic drug, wherein the neuroleptic drug is fluphenazine HCl or decanoate, haloperidol, perchlorperazine, loxapine succinate or HCl, thioridazine HCl, molindone HCl, thiothixene or its HCl, trifluoperazine HCl, chlorprothixene, its lactate and/or HCl, chlorpromazine, perphenazine and/or amitriptyline HCl and/or cholecystokinin.

16. The method as defined in claim 15 wherein the angiotensin converting enzyme inhibitor is employed in a weight ratio to the neuroleptic of within the range of from about 0.0001:1 to about 1000:1.

17. The method as defined in claim 1 wherein the angiotensin converting enzyme inhibitor is captopril, zofenopril, fosinopril, enalapril, lisinopril or (S)-1-[6-amino-2-[[hydroxy(4-phenylbutyl)phosphinyl]oxy]-1-oxohexyl-L-proline.

18. The method as defined in claim 15 wherein the angiotensin converting enzyme inhibitor is ceronapril.

19. The method as defined in claim 18 wherein ceronapril is administered systemically in an amount within the range of from about 1 to 50 mg, one to four times a day.

20. A method for treating schizophrenia in a mammalian specie, which comprises administering to a mammalian specie in need of such treatment an effective amount of an angiotensin converting enzyme inhibitor which is ceronapril in an amount within the range of from about 1 to 50 mg, one to four times a day.

* * * * *